United States Patent
Prakash et al.

(10) Patent No.: US 7,869,876 B2
(45) Date of Patent: Jan. 11, 2011

(54) METHOD AND APPARATUS FOR MONITORING AND OPTIMIZING ATRIAL FUNCTION

(75) Inventors: Rajan Prakash, Minneapolis, MN (US); Edward Chinchoy, Golden Valley, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1254 days.

(21) Appl. No.: 11/245,623

(22) Filed: Oct. 7, 2005

(65) Prior Publication Data

US 2007/0083243 A1   Apr. 12, 2007

(51) Int. Cl.
*A61N 1/368* (2006.01)
(52) U.S. Cl. .................................... 607/17
(58) Field of Classification Search ............ 600/373, 600/374, 393, 509, 513; 607/4, 5, 6, 7, 9, 607/17, 119, 122
See application file for complete search history.

(56) References Cited

U.S. PATENT DOCUMENTS

| | | | |
|---|---|---|---|
| 5,261,418 A | 11/1993 | Ferek-Petric | |
| 5,454,838 A * | 10/1995 | Vallana et al. | 607/19 |
| 5,540,727 A | 7/1996 | Tockman et al. | |
| 5,549,650 A | 8/1996 | Bornzin et al. | |
| 5,549,652 A | 8/1996 | McClure et al. | |
| 5,609,612 A * | 3/1997 | Plicchi et al. | 607/17 |
| 5,628,777 A | 5/1997 | Moberg et al. | |
| 5,693,075 A | 12/1997 | Plicchi | |
| 5,836,987 A * | 11/1998 | Baumann et al. | 607/17 |
| 5,941,904 A | 8/1999 | Johnston et al. | |
| 6,070,101 A | 5/2000 | Struble et al. | |
| 6,077,236 A | 6/2000 | Cunningham | |
| 6,223,082 B1 | 4/2001 | Bakels et al. | |
| 6,473,645 B1 | 10/2002 | Levine | |
| 7,567,838 B2 * | 7/2009 | Yu et al. | 607/9 |
| 2003/0105496 A1 | 6/2003 | Yu et al. | |
| 2004/0172078 A1 | 9/2004 | Chinchoy | |
| 2005/0027320 A1 | 2/2005 | Nehls et al. | |
| 2005/0131470 A1 | 6/2005 | Vitali et al. | |

FOREIGN PATENT DOCUMENTS

EP     0474958 A2     3/1991

OTHER PUBLICATIONS

Clementy et al., Validation by Serial Standardized testing of a new rate-responsive pacemaker based on variation in Myocardial Contractility, Europace. Apr. 2001, 3 (2):124-31.

(Continued)

*Primary Examiner*—Carl H Layno
*Assistant Examiner*—Frances P Oropeza
(74) *Attorney, Agent, or Firm*—Stephen W. Bauer; Reed A. Duthler (57) ABSTRACT

A method for use in an implantable medical device, comprising: sensing a signal corresponding to ventricular wall acceleration; and determining a metric of atrial function using the ventricular wall acceleration signal. The method includes sensing the ventricular wall acceleration signal during at least during a sensing window corresponding to a ventricular filling phase.

19 Claims, 7 Drawing Sheets

OTHER PUBLICATIONS

Leung et al, automatic Optimization of Resting and Exercise Atrioventricular Interval Using a Peak Endocardial Acceleration Sensor: Validation with Doppler Echocardiography and Direct Cardiac Output Measurements. PACE. Nov. 2000,23 (11pt2):1762-6.

Padeletti et al., Atrioventricular Interval Optimization in the Right Atrial Appendage and Interatrial Septum Pacing: a Comparison between Echo and Peak Endocardial Acceleration Measurements. PACE. Nov. 2000,23 (11pt1):1618-22.

Bordacher et al., Hemodynamic Assessment of Right Left, and Biventricullar Pacing by Peak Endocardial Acceleration and Echocardiography in Patients with End-Stage Heart Failure. PACE Nov. 2000, 23 (11pt2):1726-30.

Clementry et al., Dual Chamber Rate Responsive Pacing System Driven by Contractility:Final Assessment after 1-Year Follow-Up. the European PEA Clinical Investigation Froup. PACE. Nov. 1998,21 (11pt 2):2192-7.

Langenfeld et al., PEak Endocardial Acceleration-Based Clinical Testing of the Best DDDR Pacemaker. European PEA Clinical Investigation Group PACE Nov. 1998, 21(11pt2):2187-91.

Bongiorni et al., Is Local Myocardial Contractility Related to Endocardial Acceleration Signals Detected by a Transvenous Pacing Lead? PACE. Nov. 1996,19(11pt2):1682-8.

Rickards et al., An Implantable Intracardiac Accelerometer for Monitoring Myocardial Contractility.The Multicenter PEA Study Group. PACE. Dec. 1996, 19(12 pt 1): 2066-71.

Greco et al., Clinical Evaluation of Peak Endocardial Acceleration as a Sensor for Rate Responsive Pacing. PACE. Apr. 2003, 26(4 pt 1):812-8.

Plicchi et al., PEA I and PEA II Based Implantable Hemodynamic Monitor: Pre-Clinical Studiesin Sheep. Europace. Jan. 2002, 4(1):49-54.

International Search Report, PCT/US2006/038311, Feb. 26, 2007, 7 Pages.

* cited by examiner

METHOD AND APPARATUS FOR MONITORING AND OPTIMIZING ATRIAL FUNCTION

TECHNICAL FIELD

The invention relates generally to implantable medical devices, and, more particularly, to an implantable medical device and associated method for monitoring atrial function and optimizing atrial function during a cardiac stimulation therapy.

BACKGROUND

During normal cardiac function, the ventricles fill during two diastolic phases, a passive filling phase and an active filling phase. The passive filling phase occurs first as the ventricles relax following ventricular systole. Ventricular relaxation causes the pressure within the ventricles to fall, allowing the mitral valve between the left atrium and left ventricle and the tricuspid valve between the right atrium and right ventricle to open. Blood flows into the ventricular chambers during the passive filling phase due to the pressure difference across the mitral and tricuspid valves. As the passive filling rate slows, the atria contract, actively contributing the ventricular filling. The force generated by the actively contracting atria forces more blood into the ventricle that has already filled passively.

This atrial contribution to ventricular filling is important in maintaining an adequate preload for optimal ventricular contraction. According to the Frank-Starling law, the ventricles contract more forcefully during systole when filled to a greater degree during diastole. Generally, cardiac stroke volume increases as cardiac filling increases.

The atrial contribution to ventricular filling can become compromised during many disease states. Cardiac conditions that alter the relative timing of atrial and ventricular contraction may reduce the atrial contribution to ventricular filling, and thereby reduce the overall cardiac output. If atrial contraction occurs too late after the passive filling phase, ventricular contraction may have already begun, closing the mitral or tricuspid valves. Thus, late atrial contraction may cause the atria to contract against a closed or partially closed valve, which can result in retrograde flow. Early atrial contraction, prior to the end of the passive filling phase, results in fusion of the passive and active filling phases. The force available from the contracting atria is under utilized when blood is forced into an empty or only partially filled ventricle. Overall filling is reduced.

During a number of cardiac stimulation therapies, including dual chamber pacing, cardiac resynchronization therapy, extra-systolic stimulation, among others, an atrial-ventricular (AV) delay is set to control the timing between atrial depolarization and ventricular depolarization. The AV delay can be optimized based on various hemodynamic measurements. For example, the AV delay can be optimized using echocardiography for maximizing a measured ejection fraction or other hemodynamic or cardiac function metric. However, performing such echocardiography studies are generally time consuming and require skilled personnel to program the implantable cardiac stimulation device, such as a pacemaker or implantable cardioverter defibrillator (ICD), to multiple AV delay settings and to perform the echocardiography measurements. Furthermore, an AV delay setting determined to be optimal during an office visit may change over time with disease state or changes in patient activity level, medications or other influences. In order to achieve the full hemodynamic benefits of various cardiac stimulation therapies, it is desirable to be able to monitor atrial function such that the active, atrial contribution to ventricular filling is optimized. Monitoring the atrial function is also useful in monitoring a disease state.

DETAILED DESCRIPTION

In the following description, references are made to illustrative embodiments for carrying out the invention. It is understood that other embodiments may be utilized without departing from the scope of the invention.

Figure 1A:
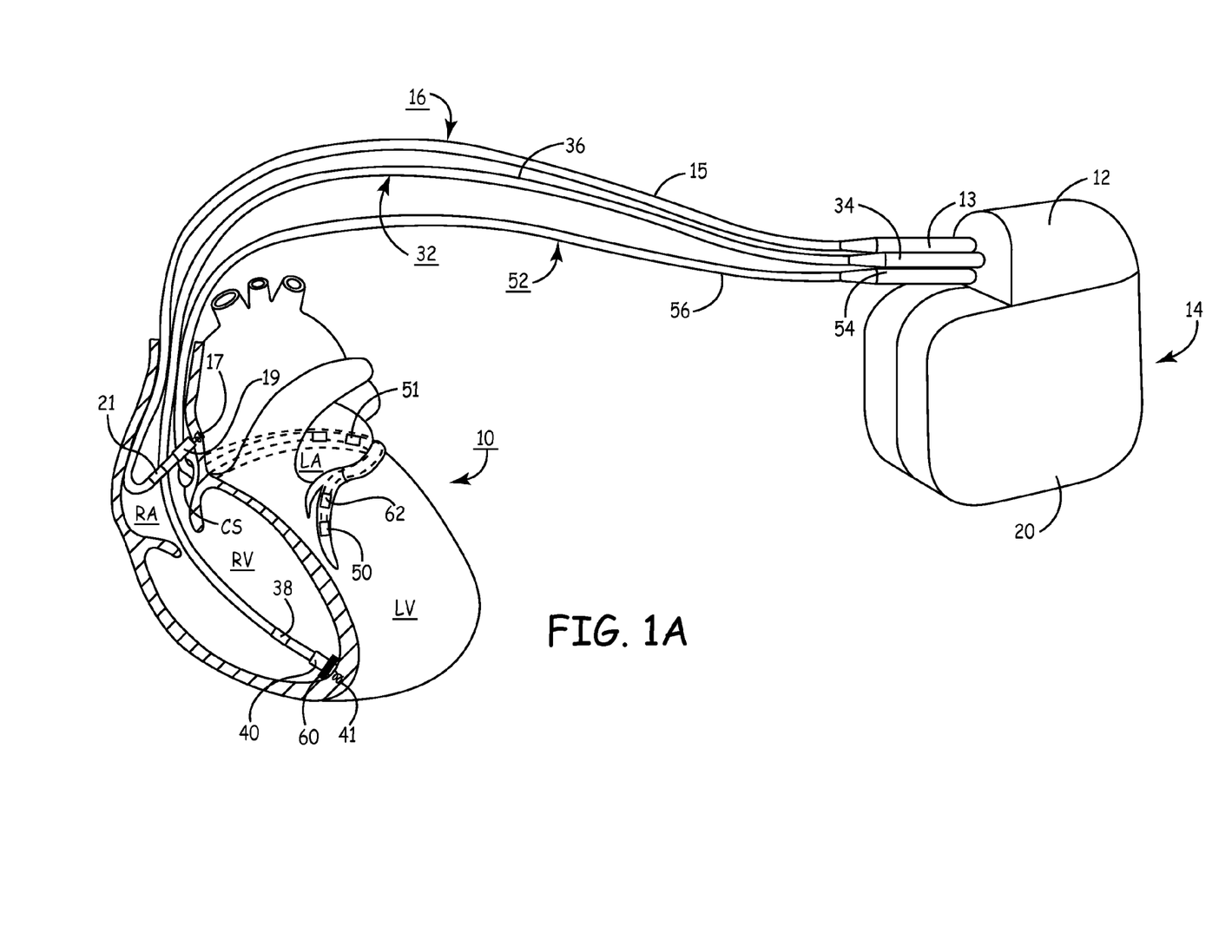
FIG. 1A depicts an implantable, multi-chamber cardiac pacemaker 14 in which one embodiment of the present invention may be implemented.

FIG. 1A depicts an implantable, multi-chamber cardiac pacemaker 14 in which one embodiment of the present invention may be implemented. The multi-chamber pacemaker 14 is provided for sensing intrinsic heart 10 activity and delivering cardiac stimulation pulses as appropriate to one or more heart chambers. Pacemaker 14 may be programmed to operate in any of a number of therapeutic stimulation modes. For example, pacemaker 14 may be configured for delivering cardiac resynchronization stimulation pulses, which control the heart activation sequence for restoring mechanical synchrony between heart chambers. In other embodiments, pacemaker 14 may deliver extra systolic stimulation pulses as needed to achieve post-extra systolic potentiation effects and thereby provide hemodynamic benefit to the patient. In various embodiments, pacemaker 14 may be configured to deliver any cardiac stimulation therapy that can be enhanced or otherwise depends on optimized atrial function to provide a beneficial effect. Although pacemaker 14 is shown as a multi-chamber pacemaker, it is understood that pacemaker 14 may be modified to operate as a dual chamber pacemaker.

Pacemaker 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins.

The pacemaker 14, also referred to herein as an "implantable pulse generator" or "IPG," is implanted subcutaneously in a patient's body between the skin and the ribs. Three transvenous endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 may be attached to the RA wall using a fixation member 17. The bipolar endocardial RA lead 16 is formed with a connector 13 fitting into a connector bore of IPG connector block 12 that is coupled to a pair of electrically insulated conductors within lead body 15 and connected with distal tip RA pace/sense electrode 19 and proximal ring RA pace/sense electrode 21 provided for achieving RA stimulation and sensing of RA electrogram (EGM) signals.

Bipolar, endocardial RV lead 32 is passed through the RA into the RV where its distal end, carrying tip RV pace/sense electrode 40 and ring RV pace/sense electrode 38, is fixed in place in the RV apex by a distal fixation member 41. The RV lead 32 is formed with a connector 34 fitting into a corresponding connector bore of IPG connector block 12 that is coupled to a pair of electrically insulated conductors within lead body 36 and connected with distal tip RV pace/sense electrode 40 and proximal ring RV pace/sense electrode 38 provided for RV stimulation and sensing of RV EGM signals. RV lead 32 may optionally include a sensor 60 responsive to RV wall acceleration. RV acceleration sensor 60 may be positioned into or proximate the RV apex for detecting acceleration of the RV apical region. In other embodiments, RV acceleration sensor 60 may be disposed at other locations along the RV for sensing RV acceleration.

Coronary sinus lead 52 is passed through the RA, into the CS and further into a cardiac vein 48 to extend the distal LV CS pace/sense electrode 50 alongside the LV chamber to achieve LV stimulation and sensing of LV EGM signals. The LV CS lead 52 is coupled at the proximal end connector 54 into a bore of IPG connector block 12. A small diameter lead body 56 is typically selected in order to lodge the distal LV CS pace/sense electrode 50 deeply in a cardiac vein branching from the great cardiac vein 48.

In one embodiment of the invention, coronary sinus lead 52 is provided with a sensor 62 capable of generating a signal proportional to the acceleration of the left ventricular free wall. Sensor 62 may be embodied as a uniaxial, biaxial, or triaxial (or multiaxial) accelerometer contained in a capsule of a relatively small size and diameter such that it may be included in a coronary sinus lead without substantially increasing the lead diameter or impairing the ability to steer the lead to a left ventricular stimulation and sensing site. For the purposes of assessing atrial function using an accelerometer deployed in operative relation to the left ventricle, a uniaxial accelerometer configured to generate a signal responsive to LV motion substantially along one axis, e.g. longitudinal acceleration, may be sufficient. Sensor 62 may alternatively be provided as another type of transducer such as a transducer having an optical, acoustical, piezoelectric, inductive, capacitive, resistive, or other elements which produce a variable signal proportional to ventricular acceleration or from which variations in ventricular acceleration can be derived.

Sensor 62 is located on CS lead 52 such that when CS lead 52 is positioned for LV stimulation and sensing, sensor 62 is located over the left ventricle and is typically positioned approximately over the left ventricular free wall mid-lateral to mid-basal segments. The depicted positions of the leads and electrodes shown in FIG. 1A in or about the right and left heart chambers are approximate and merely illustrate one of many possible configurations. For example, a left ventricular acceleration sensor 62 may alternatively be located on CS lead 52 such that sensor 62 is positioned along the great cardiac vein, or along any accessible inferior cardiac vein. Furthermore, it is recognized that alternative leads and pace/sense electrodes that are adapted for placement at stimulation or sensing sites on or in or relative to the RA, LA, RV and LV may be used in conjunction with the present invention.

In some embodiments, LV CS lead 52 could bear a proximal LA CS pace/sense electrode 51 positioned along CS lead body 56 such that it is disposed proximate the LA for use in stimulating the LA and/or sensing LA EGM signals. In that case, the lead body 56 would encase an insulated lead conductor extending proximally from the more proximal LA CS pace/sense electrode(s) and terminating at lead connector 54.

Figure 1B:
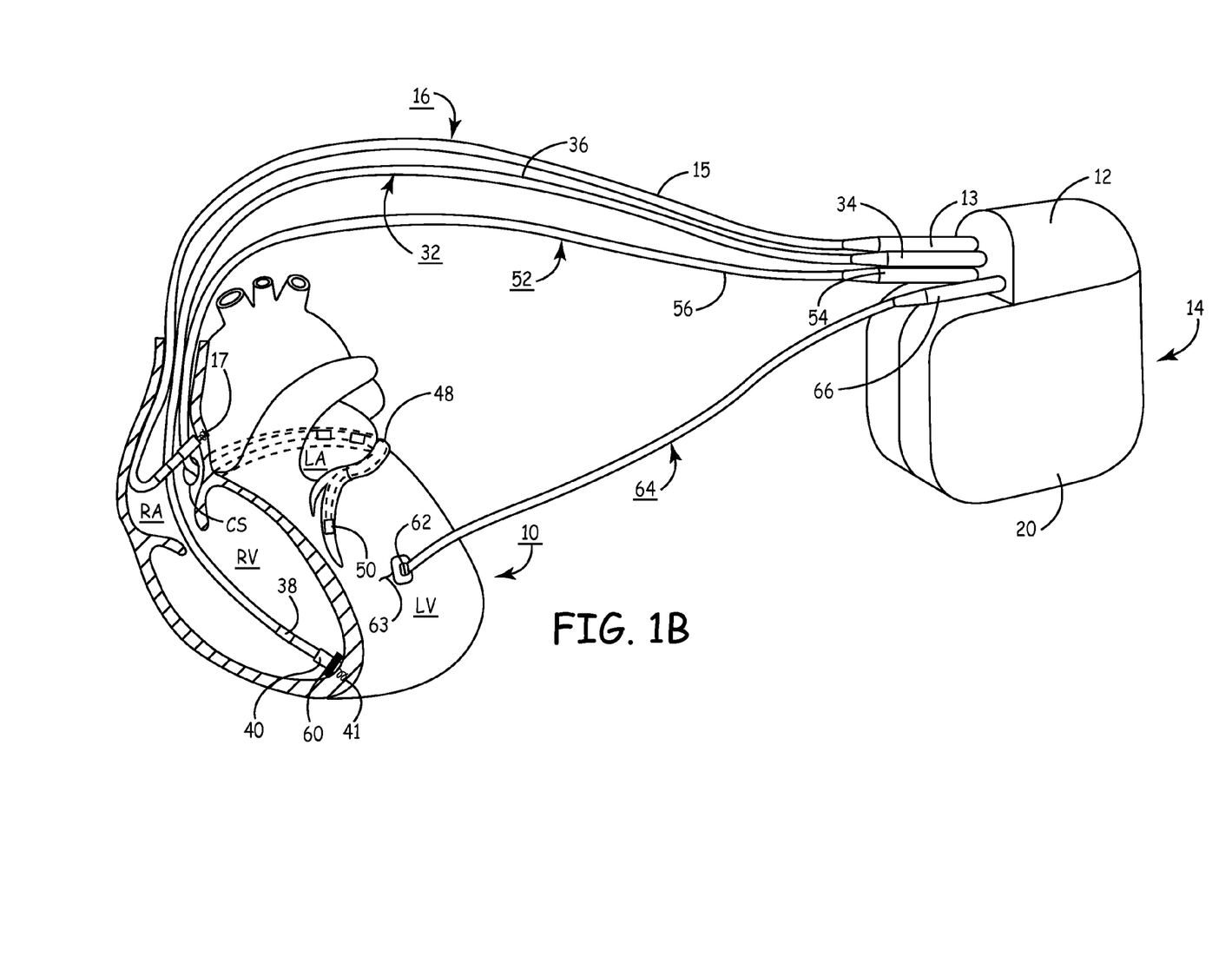
FIG. 1B depicts an implantable, multi-chamber cardiac pacemaker coupled to a patient's heart via transvenous endocardial leads and an additional left ventricular epicardial lead equipped with acceleration sensor 62.

FIG. 1B depicts an implantable, multi-chamber cardiac pacemaker coupled to a patient's heart via transvenous endocardial leads and an additional left ventricular epicardial lead equipped with acceleration sensor 62. Patients may have previously had a transvenous lead system implanted that includes a coronary sinus lead 52 that is not equipped with an acceleration sensor. Such patients may benefit from the placement of an epicardial lead 64 equipped with an acceleration sensor 62 coupled to IPG 14 via a connector 66 so as to provide an LV acceleration signal.

Epicardial lead 64 is provided with a fixation member 63 which may serve additionally as a pacing and/or sensing electrode. In some cases, an epicardial lead may be preferred over a coronary sinus lead due to the difficulty in advancing a coronary sinus lead into a relatively small cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for stimulation, EGM sensing and acceleration sensing, thereby eliminating the need for a coronary sinus lead. Alternatively, it may be desirable to deploy a small diameter coronary sinus lead for LV stimulation and EGM sensing with a separate LV epicardial lead positioned for sensing LV acceleration.

The embodiment generally shown in FIG. 1B may be used for specific selection of cardiac stimulation/sensing sites. With epicardial lead 64 fixed at a desired location for assessing LV acceleration, the effect of pacing at different locations in one or more heart chambers can be evaluated by deploying the transvenous pacing leads 16, 32 and 52 to different locations. In particular, coronary sinus lead 52 may be advanced to different locations until an optimal location is identified based on analysis of the signal from LV acceleration sensor 62. By providing acceleration sensor 62 on a separate, epicardial lead 64, the position of LV pace/sense electrode 50, provided on coronary sinus lead 52, may be adjusted independently of sensor 62. If the position of pace/sense electrode 50 needs adjusting, acceleration sensor 62 may remain fixed at a desired measurement site on the LV epicardial wall thereby allowing comparisons to be made between measurements repeated at the same location for different pacing intervals and/or pacing sites.

Any type of transducer may be provided for sensing or deriving ventricular wall acceleration corresponding to the right and/or left ventricle provided such transducers are hermetically sealed, fabricated (at least on the exterior surfaces) of substantially biocompatible materials and appropriately dimensioned for a given application. In addition to transducers that sense acceleration, transducers which sense velocity, displacement or force may be used from which an acceleration component can be derived. With respect to appropriate dimension, a transducer intended for transvenous deployment should be adapted for catheter or over-the-wire delivery. Thus, the radial dimension should generally be on the order of less than about 11 French. The transducer should be somewhat supple with a longitudinal dimension that allows the transducer to safely navigate the venous system, pass through the coronary sinus and enter vessels branching from the coronary sinus. These dimensions are less limited for a transducer intended for deployment though a portion of the chest (e.g., a thoracotomy) with a fixation mechanism adapted to mechanically coupled adjacent the epicardium or pericardium. The dimensions may be relaxed to a greater extent if the epicardial receives the transducer, and to a lesser extent, to a portion of the pericardium. As is well known, the pericardium is the membranous sac filled with serous fluid that encloses the heart and the roots of the aorta and other large blood vessels. One example of appropriate fixation apparatus for epicardial application is a lead having a distal fixation helix that is screwed into the surface of the epicardium. For pericardial fixation a sealing member (e.g., compressible gasket or opposing members on each side of the pericardial sac) may be used in addition to an active fixation member such as a helical member.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electrical signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Important characteristics of accelerometers include range of acceleration, frequency response, transverse sensitivity (i.e. sensitivity to motion in the non-active direction), mounting errors, temperature and acoustic noise sensitivity, and mass.

One type of primary transducer, which describes the internal mechanism of the accelerometer, includes a spring-retained seismic mass. In most accelerometers, acceleration forces a damped seismic mass that is restrained by a spring, so that it moves relative to the transducer casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20-60 Hz, depending on the stiffness of the spring, and have a high-level output signal. They also have a lower frequency response than most other accelerometers, usually between 15-30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capacitive accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

Figure 2:
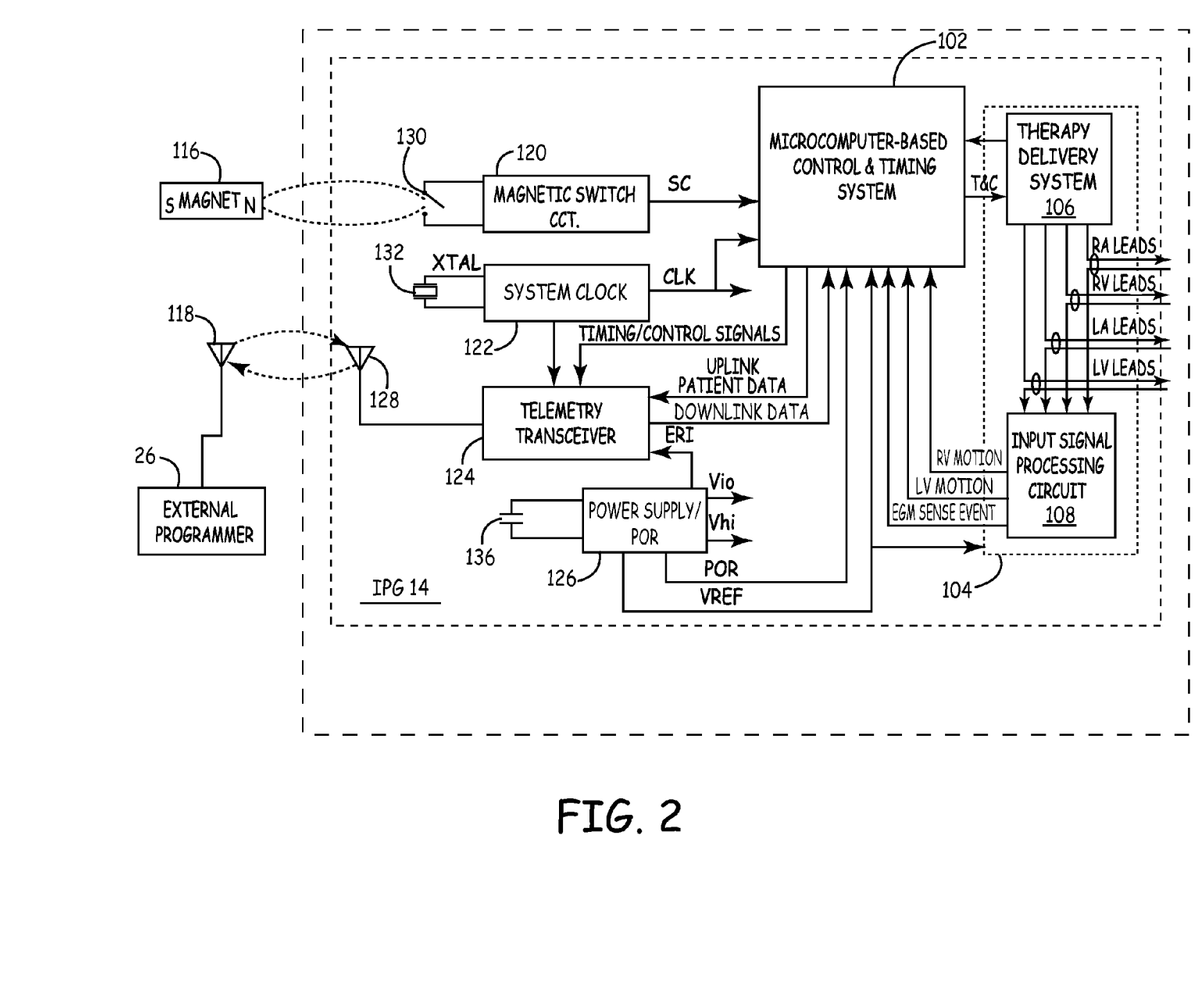
FIG. 2 is a schematic block diagram illustrating one embodiment of a multi-chamber IPG 14.

FIG. 2 is a schematic block diagram illustrating one embodiment of a multi-chamber IPG 14. IPG 14 is configured to provide a cardiac stimulation therapy and for processing ventricular acceleration signal input from any of the types of transducers described above or any other type of transducer sensitive to ventricular acceleration for use in optimizing stimulation control parameters to achieve optimal atrial function. In some embodiments, as will be described herein, IPG 14 may use a ventricular acceleration signal for monitoring atrial function without using the acceleration signal in adjusting stimulation control parameters.

As shown, IPG 14 includes a microprocessor-based control and timing system 102 for controlling the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac stimulation aimed at achieving a therapeutic benefit. The interface circuitry 104 therefore includes a therapy delivery system 106 intended for delivering cardiac stimulation pulses under the control of control and timing system 102. Delivery of stimulation pulses in one or more heart chambers is controlled in part by the selection of programmable timing intervals, which can include atrial-atrial (A-A), atrial-ventricular (A-V), and ventricular-ventricular (V-V) intervals and may further include extra systolic intervals or other timing intervals according to the type of therapy being delivered and the programmed operating mode.

Physiologic input signal processing circuit 108 is provided for receiving cardiac electrogram (EGM) signals for determining a patient's heart rhythm. Physiologic input signal processing circuit 108 additionally receives signals from left ventricular acceleration sensor 62, and/or RV acceleration sensor 60, processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV.

Control and timing system 102 controls the delivery cardiac stimulation pulses at selected timing intervals intended to improve heart function or otherwise alleviate a heart condition as needed. Selection of the programmable intervals includes an analysis of a wall acceleration signal obtained from LV acceleration sensor 62 and/or RV acceleration sensor 60 as will be described in greater detail below. In particular, a ventricular wall acceleration signal associated with the ventricular filling phase is analyzed to optimize the atrial contribution to LV filling and/or monitor atrial function.

The therapy delivery system 106 can optionally be configured to include circuitry for delivering cardioversion/defibrillation therapy in addition to cardiac pacing pulses. Accordingly, leads in communication with the patient's heart could additionally include high-voltage cardioversion or defibrillation shock electrodes.

A battery 136 provides a source of electrical energy to power components and circuitry of IPG 14 and provide energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. A power supply and interconnections with IPG 14 components may correspond to configurations known in the art.

Electronic IPG circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data, including ventricular acceleration data and data derived there from such as atrial function data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or ventricular wall acceleration data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetric communication of both analog and digital data between antenna 128 and an external device 26, also equipped with an antenna 118, may be accomplished using numerous types of telemetry systems known in the art for use in implantable devices.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an atrial sense or ventricular sense event signal to the control and timing system 102. Timing and control system 102 responds in accordance with its particular operating mode to deliver or modify a stimulation therapy, if appropriate, or to accumulate data for uplink telemetry transmission in a variety of ways known in the art. Thus the need for cardiac stimulation pulse delivery is generally determined based on EGM signal input according to the particular operating mode in effect. However, the intervals at which stimulation pulses are delivered may be determined, at least in part, based on an assessment of ventricular wall acceleration data as will be described below.

As such, input signal processing circuit 108 further includes signal processing circuitry for receiving, amplifying, filtering, averaging, digitizing or otherwise processing the LV and/or RV wall acceleration sensor signal. Acceleration signal processing circuitry is further provided for detection and/or determination of one or more acceleration signal characteristics such as maximum and minimum peak amplitudes, slopes, integrals, or other time or frequency domain signal characteristics that may be used as metrics of cardiac function, in particular as metrics of atrial function. Acceleration data from an LV wall acceleration sensor signal are made available to control and timing system 102 via LV MOTION signal line. LV acceleration data may be used for monitoring left atrial function and/or for use in algorithms performed for identifying timing intervals promoting optimal LV filling. If an RV acceleration sensor is present, an additional RV MOTION signal line provides RV acceleration signal data to control and timing system 102. RV acceleration data may be used for monitoring right atrial function and/or in algorithms performed for identifying timing intervals promoting optimal RV filling.

Figure 3:
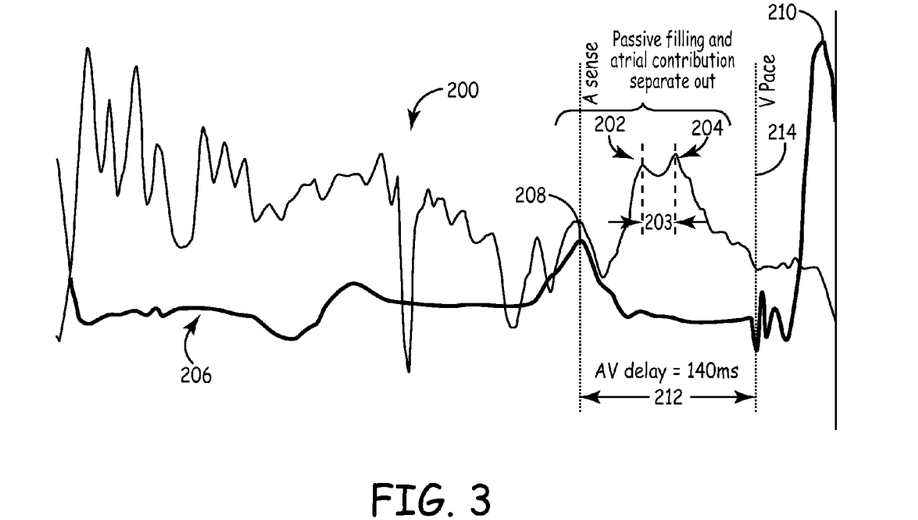
FIG. 3 is a sample LV acceleration signal illustrating the separate contribution of passive and active filling phases to LV filling.

FIG. 3 is a sample LV acceleration signal illustrating the separate contribution of passive and active filling phases to LV filling. The LV acceleration signal 200 is shown in time with respect to a simultaneously recorded ECG signal. At an optimal AV delay, passive filling occurs as the LV myocardium relaxes during a passive filling phase. At the end of LV relaxation, passive filling slows and the LA contracts, providing active filling of the LV, often referred to as the "atrial kick." During ventricular diastole, a first filling phase peak 202 corresponding to LV passive filling is distinguishable from a second filling phase peak 204 corresponding to LV active filling on the LV acceleration signal 200. The first filling phase peak 202 is separated from the second filling phase peak 204 by a time interval 203.

The LV acceleration signal may be sensed during a sensing window 212. Sensing window 212 may be initiated upon a delivered atrial pacing pulse or a sensed P-wave 208, which can be sensed using an atrial EGM signal. The atrial event used for initiating sensing window 212 may be a right atrial or left atrial event. Sensing window 212 may extend until a delivered LV pacing pulse 214 or a sensed R-wave 210 (intrinsic or evoked), which may be sensed using a ventricular EGM signal.

In the particular example shown, LV pacing pulse 214 is delivered at a 140 ms AV delay following the sensed P-wave 208. This AV delay results in optimal separation of the passive and active filling phases as indicated by separate signal peaks 202 and 204.

Figure 4:
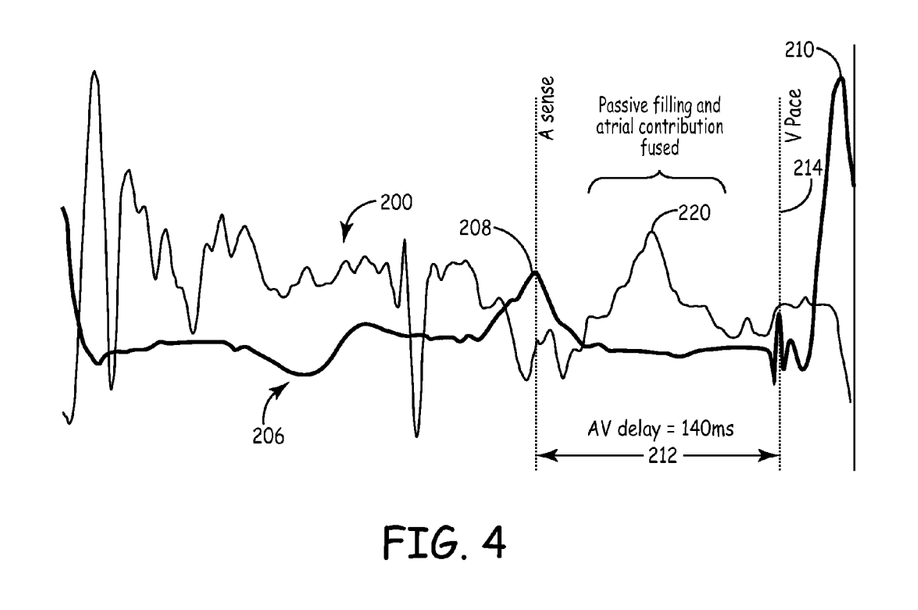
FIG. 4 is a sample LV acceleration signal illustrating fusion of ventricular passive and active filling phases.

FIG. 4 is a sample LV acceleration signal illustrating fusion of ventricular passive and active filling phases. A single filling phase peak 220 is observed on LV acceleration signal 200 during sensing window 212. The fused filling phase peak 220 occurs, in this example, when the LV pacing pulse 213 is delivered at a 180 ms AV delay following the sensed P-wave 208. At this longer AV delay, ventricular contraction and ventricular relaxation occur later in the cardiac cycle. As such, the passive filling phase associated with ventricular relaxation occurs later relative to the previous sensed or paced atrial event. The subsequent atrial event, paced or sensed, occurs prior to completion of ventricular relaxation and the passive filling phase. The "atrial kick" that occurs during passive filling to drive blood into an empty or only partially filled ventricle is underutilized. The force of the atrial contraction is better used to drive more blood into the ventricle that has already filled passively.

If the AV delay is too short, the atrium may still be contracting against the build up of pressure generated by the onset of ventricular contraction, which causes the mitral and tricuspid valves to close. As such, the active atrial filling phase will be cut short resulting in incomplete ventricular filling. Incomplete ventricular filling reduces the ventricular stroke volume according to the Frank-Starling law. As such, it is desirable to optimize the AV delay used during any cardiac stimulation therapy such that the active filling phase associated with atrial contraction occurs after passive filling and prior to the onset of the next ventricular systole to thereby maximize ventricular filling. Such optimization can be performed in a clinic using echocardiographic analysis of the E and A waves. The AV delay can be adjusted until the E wave, associated with the passive filling phase, and the A wave, associated with the active filling phase, are observed as separate peaks on a trans-mitral Doppler echocardiography image. However, it is desirable to provide an automated or semi-automated method for optimizing AV delay in an IPG. An automated method can be repeated at various time intervals to account for physiological or pathological changes over time that influence the optimal AV delay setting.

Figure 5:
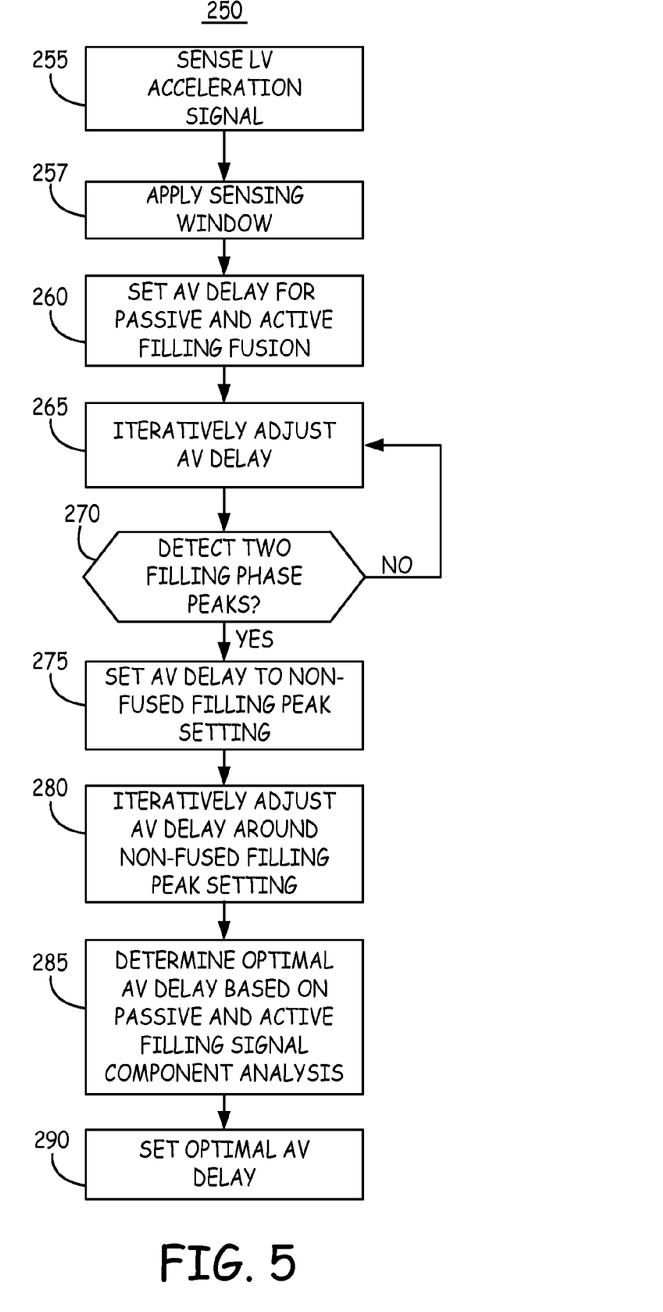
FIG. 5 is a flow chart summarizing steps included in a method for controlling AV delay based on LV acceleration signal analysis.

FIG. 5 is a flow chart summarizing steps included in a method for controlling AV delay based on LV acceleration signal analysis. While method 250 refers generally to using a LV acceleration signal for use in optimizing a left heart AV delay applied between a LA sensed P-wave or delivered stimulation pulse and a subsequent LV stimulation pulse, the method 250 can be used in right heart applications using a RV acceleration signal for optimizing a right heart AV delay. Beginning at step 255, the LV acceleration signal is sensed from an accelerometer or other appropriate transducer deployed along the LV, typically along the LV free wall.

The LV acceleration signal is sampled for atrial function analysis during a sensing window corresponding to the ventricular filling phase. In one embodiment, the sensing window is initiated upon an EGM sensed event (P-wave) or paced event in the right atrium. In another embodiment, the sensing window is initiated upon an EGM sensed event (P-wave) or a paced event in the left atrium. The sensing window may alternatively be set relative to a sensed or paced event occurring in the left ventricle. In other embodiments, the LV acceleration signal may be sensed over the entire cardiac cycle and the sensing window for atrial function analysis may be set relative to a feature of the LV acceleration signal. For example, the sensing window may be set relative to an LV acceleration peak corresponding to isovolumic relaxation or any other reference point that can be reliably detected on the acceleration signal. Alternatively, the sensing window could be set relative to other sensed signals which contain cardiac cycle information including blood pressure signals. The sensing window may be set using one or more sensed signals; the sensing window start time may be set using one sensed signal and the sensing window end time may be set using a different sensed signal. For example, the start time may be set using a sensed event on a EGM signal and the end time may be set using a fiducial point detected on the acceleration signal.

The AV delay is set at step 260 to a setting that results in a single filling phase peak occurring during the sensing window corresponding to the ventricular filling phase. Any peak detection signal analysis methods may be applied at step 260 for verifying a single, fused peak during the filling phase.

At step 265, the AV delay is adjusted to a number of AV delay settings. At each AV delay setting, the LV acceleration signal is analyzed at step 270 to determine if two separate peaks occur during the sensing window. In one embodiment, if two separate peaks occur, the AV delay is permanently set at step 275 to a value that resulted in two separate filling phase peaks, corresponding to non-fused, passive and active filling phases. Alternatively, further optimization may be performed to fine tune the AV delay, particularly if two or more AV delay settings result in separation of the passive and active filling phase peaks on the LV acceleration signal.

At step 280, iterative adjustments of the AV delay may be made around the AV delay setting first found at step 270 to produce separate passive and active filling peaks, referred to in FIG. 5 as the non-fused filling peak setting. At step 285, detailed signal analysis of the separate passive and active filling signal components is performed to determine the optimal AV delay setting. Detailed signal analysis may include, but is not limited to, determining the AV delay at which maximum temporal separation of the passive and active filling peaks occurs, or determining the AV delay at which a maximum amplitude of one or both peaks occurs.

As such, in one embodiment, the AV delay may be iteratively adjusted from a nominal or previously programmed AV delay, or a very short or very long AV delay setting, until separation of the passive and active filling phases is detected during the sensing window. The AV delay setting may be adjusted to the AV delay setting at which separation of the filling phase peaks is first observed. In another embodiment, the AV delay may be iteratively adjusted from a very short or very long setting or in a random order beginning with any nominal or previously programmed AV delay. A detailed analysis of the separate passive and active filling peaks (when they occur) is performed to determine the optimal AV delay setting among all settings that result in separate peaks.

In yet another embodiment, the AV delay may be iteratively adjusted until separation of the passive and active filling peaks is detected. Further adjustments to AV delay are made in smaller increments around the AV delay setting at which non-fused filling phases were first detected. A more detailed signal analysis of the passive and active filling peaks is performed at each setting to determine an optimal AV delay. It is recognized that numerous variations of an algorithm may be conceived for optimizing AV delay using a ventricular acceleration signal for detecting the separation of the passive and active filling phases. Such methods may include performing more detailed analyses of the passive and active filling phase signals.

It is further recognized that method 250 is not limited to an acceleration signal analysis that includes detecting signal peaks associated with the passive and active filling phases. Other signal features could be used for differentiating fused and distinct active and passive filling phases. Other signal features that may be used for detecting separate active and passive filling phases may include, but are not limited to, signal slopes, inflection points, and morphological signatures. Acceleration signal analysis for optimizing AV delay may therefore include analysis of any aspect of the acceleration signal associated with atrial filling.

Method 250 for optimizing an AV delay may be applied during different pacing modes such that unique AV delay settings are determined for different pacing modes. For example, one optimal AV delay may be determined during atrial sensing and a second optimal AV delay may be determined during atrial pacing. Unique AV delay settings may be determined for use during extra-systolic stimulation, cardiac resynchronization therapy, DDD pacing, etc. Unique AV delays corresponding to different pacing modes may be determined and stored for use by the device in controlling stimulation pulse delivery.

Figure 6:
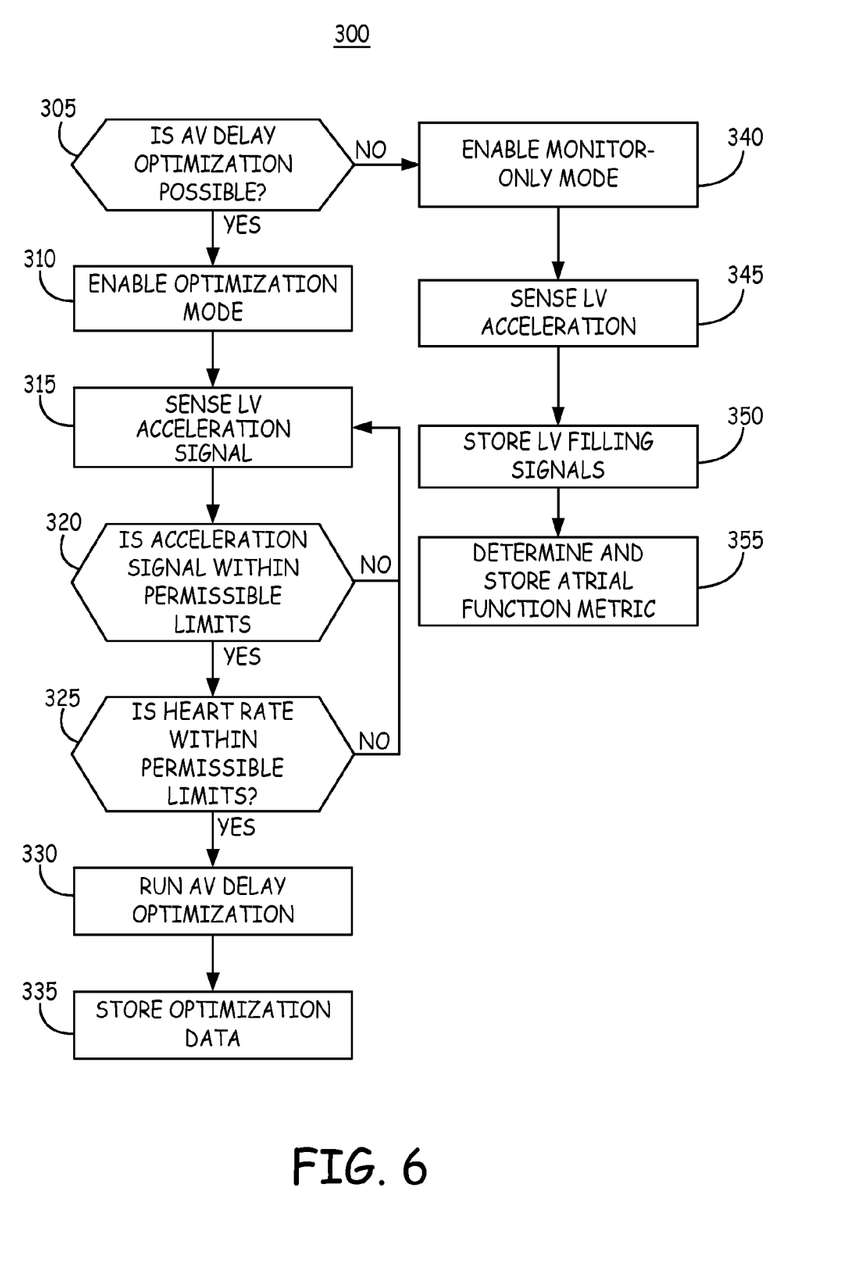
FIG. 6 is a flow chart summarizing a method for monitoring atrial function based on a ventricular acceleration signal.

FIG. 6 is a flow chart summarizing a method for monitoring atrial function based on a ventricular acceleration signal. In some applications, LA function may be monitored using the LV acceleration signal with or without optimization of an AV delay. While FIG. 6 refers generally to monitoring LA function, it is recognized that method 300 may be applied for monitoring RA function using a RV acceleration signal. At decision step 305, a determination is made whether AV delay optimization is possible. Atrial fibrillation, atrial tachycardia or other confounding physiologic or pathophysiologic conditions may be present preventing application of an optimized AV delay in some patients. AV delay may not be a control parameter in use by the IPG depending on the operating mode or type of therapy being delivered. As such, AV delay optimization may not be feasible in all patients at all times. If AV delay optimization is determined to be possible at step 305, an optimization mode is enabled at step 310.

The LV acceleration signal is sensed at step 315. An evaluation of the LV acceleration signal may be performed at decision step 320 to verify that the signal is stable for reliable comparisons of the sensed signal at different AV delay settings. If the acceleration signal amplitude is within predefined limits or meets other signal stability criteria, a stable heart rate may be verified at step 325. If the heart rate is fluctuating or crossing a predetermined rate limit, the optimization method results may not be reliable or may not be relevant at a different, stable heart rate. If either of the acceleration signal stability or the heart rate stability criteria are not met, method 300 returns to step 315 and continues sensing the LV acceleration signal until the stability criteria are met.

At step 330, an AV delay optimization algorithm is performed, as described above in conjunction with FIG. 5. After optimizing the AV delay setting, optimization data may be stored at step 335. Optimization data may include: sensed LV acceleration signals; one or more atrial function metrics derived from the LV acceleration signal; date and time information, heart rate, posture, activity level and any other relevant data. Among the atrial function metrics that may be derived from the LV acceleration signal are a passive filling peak amplitude, an active filling peak amplitude, the ratio of the passive and active filling peak amplitudes, or the time separation between passive and active filling peaks. Other aspects of the acceleration signal associated with the filling phases, other than signal peaks, may alternatively or additionally be used and stored including, but not limited to, morphological signatures, slopes, inflections points, or any other signal feature.

If AV delay optimization is not possible, as determined at decision step 305, a monitoring-only mode is enabled at step 340. The LV acceleration signal is sensed at step 345. The LV acceleration signal may be sampled during a predefined sensing window corresponding to the filling phase, and these signals may be stored at step 350 for later transmission to an external device. The LV acceleration signal may be analyzed for determining one or more atrial function metrics at step 355. Atrial function metrics and/or LV acceleration signal data may be stored along with any other relevant data for later transmission to an external device.

Thus, a method and apparatus for monitoring atrial function and optimizing an AV delay have been presented in the foregoing description with reference to specific embodiments. It is appreciated that various modifications to the referenced embodiments may be made without departing from the scope of the invention as set forth in the following claims.

The invention claimed is:

1. A method for use in an implantable medical device, comprising:
   sensing a signal corresponding to ventricular wall acceleration during a ventricular filling phase; and
   determining a metric of atrial function using the ventricular wall acceleration signal sensed during the ventricular filling phase, wherein sensing the ventricular wall acceleration signal includes sensing a signal corresponding to left ventricular wall acceleration.

2. A method according to claim 1 wherein the medical device comprises a cardiac pacemaker, and further comprising:
   delivering pacing pulses on expirations of pacing intervals; and
   adjusting durations of the pacing intervals responsive to the determined metric of atrial function.

3. A method according to claim 1 wherein the medical device comprises a cardiac pacemaker, and further comprising:
   delivering ventricular pacing pulses on expirations of AV intervals; and
   adjusting durations of the AV intervals responsive to the determined metric of atrial function.

4. A method for use in an implantable medical device, comprising:
   sensing a signal corresponding to ventricular wall acceleration during a ventricular filling phase; and
   determining a metric of atrial function using the ventricular wall acceleration signal sensed during the ventricular filling phase, wherein determining a metric of atrial function includes detecting a first ventricular filling phase peak during the ventricular filling phase and detecting if a second ventricular filling phase peak during the ventricular filling phase follows the first ventricular filling phase peak.

5. A method according to claim 4 wherein the medical device comprises a cardiac pacemaker, and further comprising:
   delivering pacing pulses on expirations of pacing intervals; and
   adjusting durations of the pacing intervals responsive to the detection of a second ventricular filling phase peak.

6. A method according to claim 4 wherein the medical device comprises a cardiac pacemaker, and further comprising:
   delivering ventricular pacing pulses on expirations of AV intervals; and
   adjusting durations of the AV intervals responsive to the detection of a second ventricular filling phase peak.

7. A method for use in an implantable medical device, comprising:
   sensing a signal corresponding to ventricular wall acceleration during a ventricular filling phase; and
   determining a metric of atrial function using the ventricular wall acceleration signal sensed during the ventricular filling phase, wherein determining a metric of atrial function includes determining a time interval between a first ventricular filling phase peak and a second ventricular filling phase peak during the ventricular filling phase.

8. A method according to claim 7 wherein the medical device comprises a cardiac pacemaker, and further comprising:
   delivering pacing pulses on expirations of pacing intervals; and
   adjusting durations of the pacing intervals responsive to the determined time interval.

9. A method according to claim 7 wherein the medical device comprises a cardiac pacemaker, and further comprising:
   delivering ventricular pacing pulses on expirations of AV intervals; and
   adjusting durations of the AV intervals responsive to the determined time interval.

10. An implantable medical device comprising:
    means for generating a signal corresponding to ventricular wall acceleration during a ventricular filling phase;
    means for receiving the signal from the generating means;
    means for deriving a metric of atrial function using the acceleration signal sensed during the ventricular filling phase; and
    means for storing the atrial function metric, wherein the means for deriving the atrial function metric includes means for detecting a first ventricular filling phase peak during the ventricular filling phase and means for detecting if a second ventricular filling phase peak during the ventricular filling phase follows the first ventricular filling phase peak.

11. A device according to claim 10, further comprising:
    means for delivering pacing pulses on expirations of pacing intervals; and
    means for adjusting durations of the pacing intervals responsive to the detection of a second ventricular filling phase peak.

12. A device according to claim 10, further comprising:
    means for delivering ventricular pacing pulses on expirations of AV intervals; and
    means for adjusting durations of the AV intervals responsive to the detection of a second ventricular filling phase peak.

13. An implantable medical device comprising:
    means for generating a signal corresponding to ventricular wall acceleration during a ventricular filling phase;

means for receiving the signal from the generating means;

means for deriving a metric of atrial function using the acceleration signal sensed during the ventricular filling phase; and means for storing the atrial function metric, wherein the means for deriving the atrial function metric includes means for determining a time interval between a first ventricular filling phase peak during the ventricular filling phase and a second ventricular filling phase peak during the ventricular filling phase.

14. A non-transitory computer readable medium storing a set of instructions which when implemented in an implantable medical device system cause the system to:

sense a signal corresponding to ventricular wall acceleration during a ventricular filling phase;

determine a metric of atrial function using the ventricular wall acceleration signal sensed during the ventricular filling phase, wherein the instructions for determining a metric of atrial function include:

instructions for detecting a first ventricular filling phase peak during the ventricular filling phase; and instructions for detecting if a second ventricular filling phase peak during the ventricular filling phase follows the first ventricular filling phase peak.

15. A medium according to claim 14, further storing instructions which when implemented in an implantable medical device system cause the system to:

deliver pacing pulses on expirations of pacing intervals; and adjust durations of the pacing intervals responsive to the determined time interval.

16. A medium according to claim 14, further storing instructions which when implemented in an implantable medical device system cause the system to:

deliver ventricular pacing pulses on expirations of AV intervals; and adjust durations of the AV intervals responsive to the determined time interval.

17. A non-transitory computer readable medium storing a set of instructions which when implemented in an implantable medical device system cause the system to:

sense a signal corresponding to ventricular wall acceleration during a ventricular filling phase; and determine a metric of atrial function using the ventricular wall acceleration signal sensed during the ventricular filling phase, wherein the instructions for determining a metric of atrial function include instructions for determining a time interval between a first ventricular filling phase peak during the ventricular filling phase and a second ventricular filling phase peak during the ventricular filling phase.

18. A medium according to claim 17, further storing instructions which when implemented in an implantable medical device system cause the system to:

deliver pacing pulses on expirations of pacing intervals; and adjust durations of the pacing intervals responsive to the detection of a second ventricular filling phase peak.

19. A medium according to claim 17, further storing instructions which when implemented in an implantable medical device system cause the system to:

deliver ventricular pacing pulses on expirations of AV intervals; and adjust durations of the AV intervals responsive to the detection of a second ventricular filling phase peak.

* * * * *